United States Patent
Koo et al.

(10) Patent No.: US 7,330,252 B2
(45) Date of Patent: Feb. 12, 2008

(54) POROUS SILICON ON-CHIP SPECTROSCOPY SYSTEM

(75) Inventors: Tae-Woong Koo, Cupertino, CA (US); Selena Chan, Sunnyvale, CA (US)

(73) Assignee: Intel Corporation, Santa Clara, CA (US)

(\*) Notice: Subject to any disclaimer, the term of this patent is extended or adjusted under 35 U.S.C. 154(b) by 118 days.

(21) Appl. No.: 11/325,832

(22) Filed: Dec. 30, 2005

(65) Prior Publication Data
US 2007/0153266 A1 Jul. 5, 2007

(51) Int. Cl.
*G01J 3/44* (2006.01)
*G01N 21/64* (2006.01)
*G01N 21/65* (2006.01)

(52) U.S. Cl. .................. 356/301; 356/317; 356/417; 250/458.1

(58) Field of Classification Search .............. 356/301, 356/417
See application file for complete search history.

(56) References Cited

U.S. PATENT DOCUMENTS 7,226,733 B2 \* 6/2007 Chan et al. ................ 435/6

OTHER PUBLICATIONS

Kuzik et al., Raman scattering enhancement in porous silicon microcavity, Applied Physics Letters, vol. 75, No. 13, Sep. 27, 1999, pp. 1830-1832.\*
Stephan Frohnoff, et al., "Porous Silicon Superlattices", Advanced Materials, vol. 6, No. 12 (1994) [pp. 963-965].
M. G. Berger, et al., "Porosity Superlattices: A New Class of Si Heterostructures", J. Phys. Appl. Phys. 27 (1994) [pp. 1333-1336].
M. G. Berger, et al., "Investigation and Design of Optical Properties of Porosity Superlattices", Thin Solid Films 255 (1995) [pp. 313-316].
Selena Chan, et al., "Tunable, Narrow, and Directional Luminescence From Porous Silicon Light Emitting Devices", Applied Physics Letters, vol. 75, No. 2, Jul. 12, 1999 [pp. 274-276].

\* cited by examiner

*Primary Examiner*—F. L. Evans
(74) *Attorney, Agent, or Firm*—Julia A. Hodge

(57) ABSTRACT

Embodiments of the present invention provide a miniaturized spectroscopy system comprising a light source fabricated from porous silicon. Porous silicon light emitting devices can provide tunable, narrow, and directional luminescence. Advantageously, a porous silicon light source can be integrated into a silicon wafer based device thus simplifying the manufacture of a miniaturized spectros copy system and lab-on-a-chip type devices employing spectroscopic detection.

21 Claims, 6 Drawing Sheets

POROUS SILICON ON-CHIP SPECTROSCOPY SYSTEM

BACKGROUND OF THE INVENTION

1. Field of the Invention

The embodiments of the present invention relate generally to miniaturized spectroscopy systems and porous silicon light sources.

2. Background Information

The ability to detect and identify trace quantities of analytes has become increasingly important in many scientific disciplines, ranging from part per billion analyses of pollutants in sub-surface water to analysis of treatment drugs and metabolites in blood serum. Additionally, the ability to perform assays in multiplex fashion greatly enhances the rate at which information can be acquired. Devices and methods that accelerate the processes of elucidating the causes of disease, creating predictive and/or diagnostic assays, and developing effective therapeutic treatments are valuable scientific tools.

Among the many techniques that can be used for chemical analyses, surface-enhanced Raman spectroscopy (SERS) has proven to be a sensitive method. A Raman spectrum, similar to an infrared spectrum, consists of a wavelength distribution of bands corresponding to molecular vibrations specific to the sample being analyzed (the analyte). Raman spectroscopy probes vibrational modes of a molecule and the resulting spectrum, similar to an infrared spectrum, is fingerprint-like in nature. As compared to the fluorescent spectrum of a molecule which normally has a single peak exhibiting a half peak width of tens of nanometers to hundreds of nanometers, a Raman spectrum has multiple structure-related peaks with half peak widths as small as a few nanometers.

The development of new classes of nano-reporters for molecular detection and biological assays, such as for example, composite organic inorganic nanoclusters (COINS), has driven the need, in part, for increasingly miniaturized and cost-effective spectroscopy systems to take advantage of a variety of possible applications of these nano-particle reporters. COINs are composed of metal nanoparticle clusters and at least one organic Raman-active compound. Interactions between the metal of the clusters and the Raman-active compound(s) enhance the Raman signal obtained from the Raman-active compound(s) when the nanoparticle is excited by a laser.

Currently, most Raman spectroscopy systems are benchtop devices. Such devices are typically comprised of expensive components such as: a laser excitation source, a microscope and other optics, a spectrometer, and a large detector. The size and cost of these Raman systems can function as a prohibitive barrier to applications of nanoparticle reporters such as COINs. Miniaturized spectroscopy systems potentially have applications, for example, as elements of field, home, and office diagnostic tests for medical and environmental testing and monitoring.

To obtain a Raman spectrum, typically a beam from a light source, such as a laser, is focused on the sample generating inelastically scattered radiation which is optically collected and directed into a wavelength-dispersive spectrometer. Although Raman scattering is a relatively low probability event, SERS can be used to enhance signal intensity in the resulting vibrational spectrum. Enhancement techniques make it possible to obtain a $10^6$ to $10^{14}$ fold Raman signal enhancement.

DETAILED DESCRIPTION OF THE INVENTION

Figure 1:
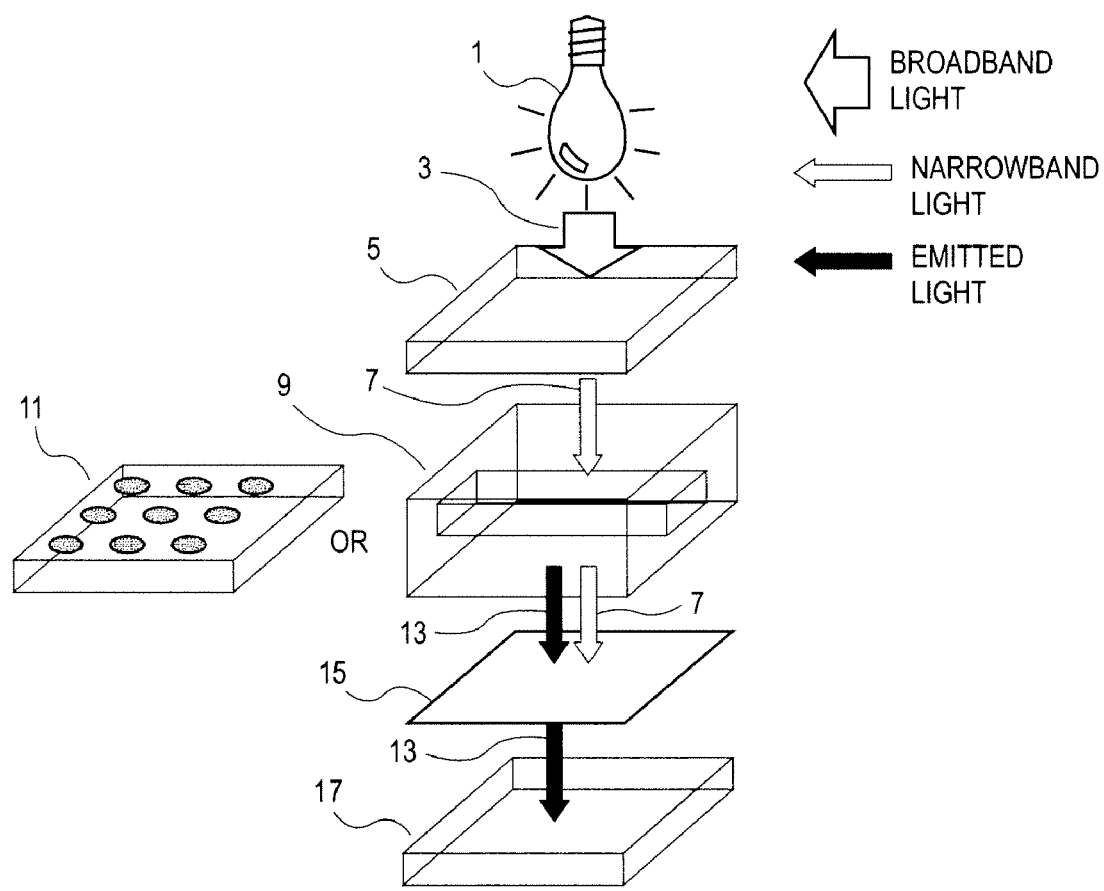
FIG. 1 diagrams a generalized configuration for a miniaturized spectroscopy system employing a porous silicon light source.

Embodiments of the present invention provide miniaturized spectroscopy systems that employ porous silicon devices as light sources. Porous silicon light emitting devices can provide tunable, narrow, and directional luminescence. Porous silicon light emitting devices can be integrated onto a silicon wafer based device thus potentially simplifying the design and manufacture of miniaturized spectroscopy systems. Such miniaturized spectroscopy systems are useful, for example, for detecting small quantities of analytes and as components of lab-on-a-chip type devices. FIG. 1 provides a general schematic for a spectroscopy system incorporating a porous silicon light source.

Porous Silicon Light Sources

Figure 2:
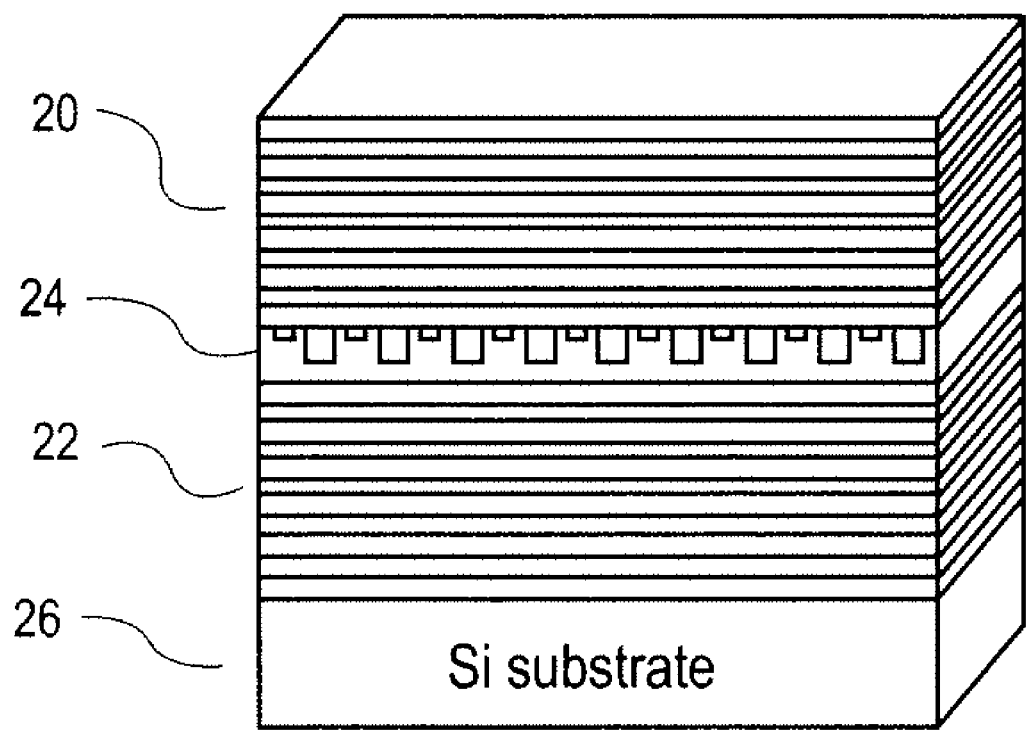
FIG. 2 shows an exemplary porous silicon microcavity resonator.

Controlled room-temperature photoluminescence and electroluminescence from porous silicon multilayer structures has been achieved. See, for example, Chan, S., Fauchet, P. M., *App. Phys. Lett.*, 75:274 (1999). Referring now to FIG. 2, the basic structure of an exemplary porous silicon light emitting device is composed of two porous silicon multilayer mirrors 20 and 22 sandwiching a highly luminescent porous silicon film 24 on a silicon substrate 26. Incorporating a thin highly luminescent porous silicon layer 24 between two multilayer mirrors 20 and 22 creates a Fabry-Perot cavity and leads to a dramatic decrease in luminescence line-width and the confined mode of emission can be tuned by changing the refractive index of the active layer 24. The decrease in luminescence line width is on the order of from a line width of about 150 nm for single layer of porous polysilicon to less than about 20 nm for porous silicon sandwich device.

Porous silicon structures can also be fabricated to function as interference filters and multilayer mirrors. See, for example, Berger, M. G. et al., *Thin Solid Films*, 255:313 (1995); Berger, M. G. et al, *J. Phys. D*, 27:1333 (1994); Frohnhoff, S. and Berger, M. G., *Adv. Mat.*, 6:963 (1994). In the case of porous silicon mirrors, it is possible to control the multilayer mirror structure's reflectivity spectrum by selecting the thickness and refractive index of each layer. A large difference in refractive indices of the single layers provides mirrors that exhibit a high degree of reflectivity. The refractive index of a porous silicon material is dependent on the porosity of the material. A wide range of porosities can be achieved for silicon materials, such as for example, 30% to 95% for highly boron-doped silicon (p+, 0.008-0.01 Ωcm), and using an effective medium approximation, this range of porosities yields values of refractive indexes from 2.69 to 1.06.

Light emission from porous silicon occurs mainly in the visible region of the electromagnetic spectrum. The wavelength of the emitted light can be changed by increasing or decreasing the porosity of the material. For example, a highly porous sample (about 70 to about 80% porosity) will emit green/blue light while a less porous sample (about 40% porosity) will emit red light. Typically, the porous silicon microcavity can absorb the broadband light emitted by, for example, a green or blue LED (light emitting diode), a xenon lamp, or a mercury lamp, and emit light within a narrow wavelength band. In general, porous silicon emitters useful in embodiments of the present invention can be comprised of layers of porous silicon and or other porous materials having different properties, such as, for example, different indexes of refraction.

Figure 3:
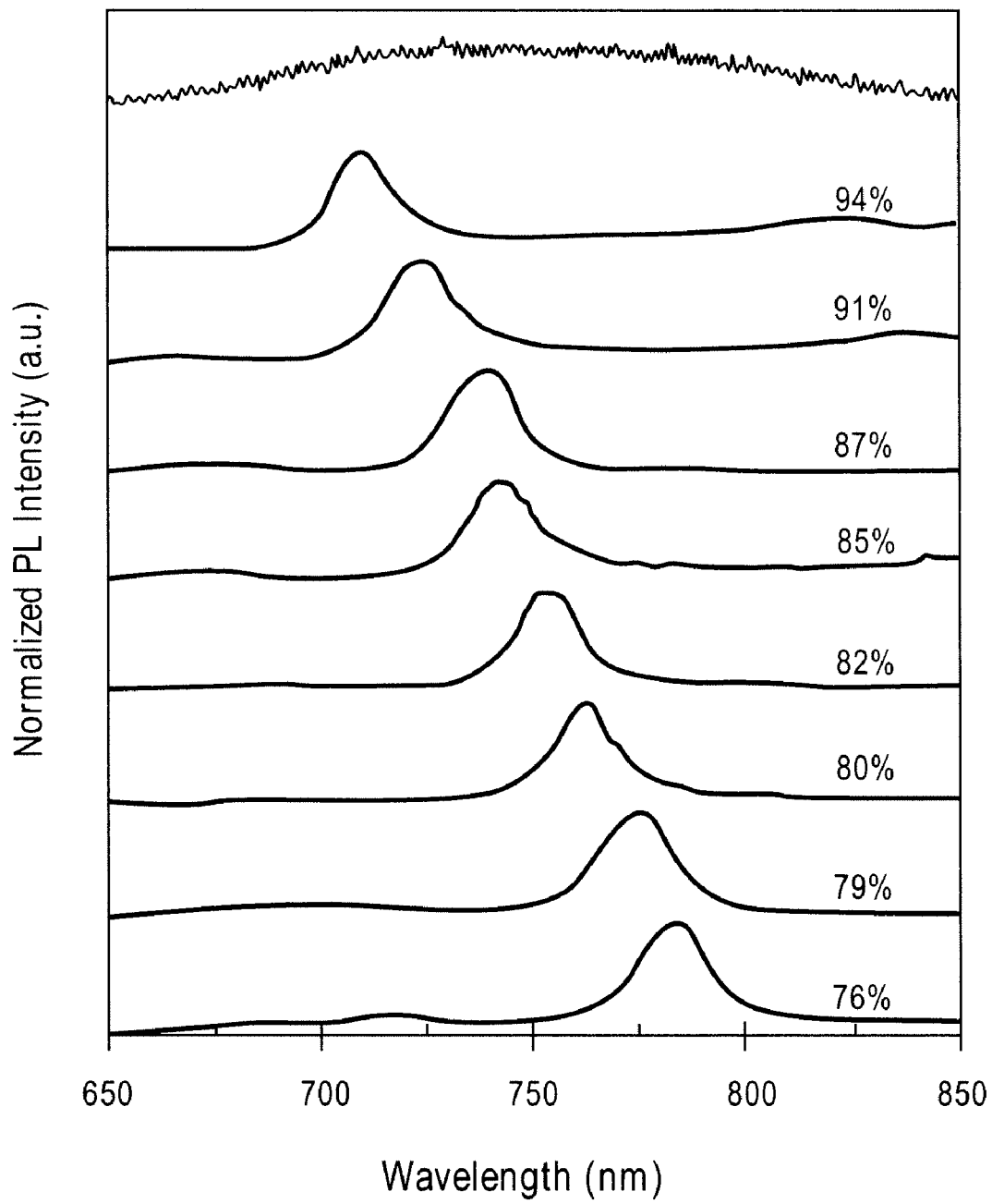
FIG. 3 shows the luminescence spectra obtained from a porous silicon microcavity resonators having active layers with porosities varying from 76% to 94%.

Referring to FIG. 3, room temperature photo-luminescence (PL) spectra are provided for porous silicon microcavity resonators having active layer porosities of between 76% and 94%. Average porosity values are labeled next to their respective photoluminescence spectra. For reference the top spectrum is a photoluminescence spectrum obtained from a single active layer having a porosity of about 80%. Spectra were obtained using the 514 nm excitation of an $Ar^+$ ion laser and detected with an optical multichannel analyzer detector. As can be seen from the spectra, wavelengths for emission obtained varied from 780 nm to 700 nm. The multilayer mirrors sandwiching the active layer contained six periods of 43% and 62% porosity layers and the porosity layers had thicknesses of 80 nm and 160 nm, respectively. The device was formed from highly boron-doped silicon ($p^+$, 0.008-0.01 $\Omega$cm). The active layer was comprised of an active, highly luminescent porous silicon layer that had an approximate thickness of about 150 nm.

Suitable porous materials include porous silicon (e.g., single crystal porous silicon), porous polysilicon, porous ceramics (e.g., those made from fibrous porous silicon nitride), porous silica, porous alumina, porous silicon-germanium, porous germanium, porous gallium arsenide, porous gallium phosphide, porous zinc oxide, and porous silicon carbide. Methods of making such porous materials are generally known by those having ordinary skill in the art. See, for example, Dougherty et al. (2002) *Mat. Res. Soc. Symp. Proc.* 687:B.7.3.1-B.7.3.6 (porous polysilicon), Ohji (2001) *AIST Today* 1:28-31 (porous ceramics), Trau et al. (1997) *Nature* 390:674-676 (porous silica), Masuda et al. (1995) *Science* 268:1466-1468 (porous alumina), Li et al. (1999) *Adv. Mater.* 11:483-487 (porous alumina), Nielsch et al. (2000) *Adv. Mater.* 12:582-586 (porous alumina), Buttard et al. (1997) *Thin Solid Films* 297:233-236 (porous silicon-germanium), van Vugt et al. (2002) *Chem Commun.* 2002: 2054-2055 (porous germanium), Kamenev et al. (2000) *Semiconductors* 34:728-731 (porous gallium arsenide), Buzynin et al. (2000) *Tech. Physics* 45:650-652 (porous gallium arsenide), Shuurmans et al. (1999) *Science* 284:141-143 (porous gallium phosphide), Lubberhuizen et al. (2000) *J. Porous Mat.* 7:147-152 (porous gallium phosphide), Terada et al. (1999) *4th Int'l. Conf on Ecomaterials*, P-30: 559-562 (porous zinc oxide), Jessensky et al. (1997) *Thin Solid Films* 297:224-228 (porous silicon carbide), Spanier et al. (2000) *Appl. Phys. Lett.* 76:3879-3881 (porous silicon carbide), Spanier et al (2000) *Physical Review B* 61:10437-10450 (porous silicon carbide), and Sangsig et al. (2000) *Jpn. J Appl. Phys.* 39:5875-5878 (porous silicon carbide). The substrate can include a plurality of layers of the porous material.

The structure also can include other materials adjacent to the substrate, such as metals, crystals, polymers, and optical glass. Suitable metals include, but are not limited to, aluminum, copper, gold, iridium, nickel, palladium, platinum, rhodium, silver, steel, titanium, tungsten, zinc, and alloys thereof. Having a metal layer on the porous silicon emitting device, allows electroluminescent emission to be obtained from the device. Suitable crystals include, but are not limited to, magnesium fluoride, calcium fluoride, quartz, diamond, sapphire, germanium, and ZnSe. Suitable polymers include, but are not limited to, polydimethylsiloxane (PDMS) and plastics. Suitable optical glass materials include those commercially available from, for example, Schott Glass (Germany) under the names BK7, SFL11, BaK4, F2, SK5, SF2, SF1, and LASF35. Additional, suitable optical glass materials include, but are not limited to, crown, flint, soda lime glass, flat glass, and borosilicate glass. Any one or more of the foregoing materials may be a part of the structure depending upon the handling and/or structural integrity characteristics desired of the structure.

As observed by high resolution scanning and transmission electron microscope, porous silicon typically has pore diameters varying from a few nanometers to several micrometers, depending upon the conditions under which the porous silicon was formed. The term "porous" as used herein may be defined consistent with the IUPAC guidelines, wherein "microporous" refers to pores having a size regime that is less than or equal to two nanometers (nm), "mesoporous" refers to pores having a size regime that is between about 2 and 50 nm, and "macroporous" refers to pores having a size regime that is greater than about 50 nm. See e.g., Cullis et al. (1997) *J. Appl. Phys. Rev.* 82:909-965.

The nature of the substrate disclosed herein is characterized by its "porosity," i.e., the relative volume fraction occupied by the pores (expressed as a percentage of the total volume of silicon and pores). Depending upon the wafer and the manufacturing conditions, the morphology of the porous material can be either "sponge-like" or "columnar." Where the morphology is "sponge-like," pores having dimensions that range from several microns in width to only a few nanometers are randomly distributed in the film. The pores are defined by crystalline walls anchored to the floor of the wafer. Micron-sized pores also may be columnar. Where the morphology is "columnar," there are long pores of typically 15 nm diameter defined by walls approximately running parallel to the <100> direction of the lattice, wherein the walls have a thickness of less than about 20 nm, and preferably about 5 nm to about 10 nm. The size and orientation of the pores can be controlled by the etching conditions. However, virtually all porous layers will exhibit some non-homogeneity with depth, i.e., a finite porosity gradient exists. Porous layers may exhibit a negative porosity gradient depending on the etching conditions, i.e., the porosity will decrease with increasing depth within the layer, and is highest at its surface.

Porous materials, such as porous silicon, may be made by many different techniques, the most common of which is one using electrochemistry because a relatively large and relatively homogeneous substrate can be readily formed by such technique. Additionally, porous silicon can be prepared by a variety of techniques, such as, for example, stain etching and anodic etching. Anodic electrochemical etching permits one to carefully control properties of the formed substrate such as, for example, microstructure, pore diameter, porosity, refractive index, and thickness. Anodic electrochemical etching includes immersing an electrode (e.g., a platinum electrode) and a silicon wafer in an electrolytic bath containing, for example, water, ethanol, and hydrofluoric acid (HF), or solutions of hydrogen nitrate ($HNO_3$) in HF. While in solution, the wafer is subjected to a constant current in a range of about 1 $mA/cm^2$ to about 1000 $mA/cm^2$, preferably about 5 $mA/cm^2$ to about 500 $mA/cm^2$. The cuurent is applied to the wafer for a time period ranging from several seconds to several hours, preferably for up to about one hour, to form a layer of porous silicon at or on the surface of the wafer. Etching and anodization can occur with or without illumination depending upon the type of substrate dopant. After anodization, the porous wafer is removed, rinsed, and dried leaving a porous silicon layer etched into the wafer. Drying may occur by way of atmospheric drying, nitrogen gas drying, supercritical drying, freeze drying, or by polymerization of pore liquids. To ensure that the morphology of the formed substrate remains intact, the substrate should be stored in vacuum, under an inert atmosphere, or under such other conditions so as not to affect the morphology. Reproducibility and the electronic, optical, and structural characteristics of the formed porous silicon are dependent upon various processing conditions, such as, for example, the electrolyte composition and temperature, current density, the applied current, and the resistivity of the wafer.

With respect to the electrolyte composition, ethanol is commonly added to the HF to minimize hydrogen bubble formation during anodization and, thus, improves layer uniformity. Ethanol also improves wettability and helps HF to better infiltrate into the pores. Electrolyte compositions containing dilute HF typically will provide layers having high porosity, while electrolyte compositions containing concentrated HF typically will provide layers having low porosity. The electrolyte preferably is at room temperature, such as, for example, about 15° C. to about 25° C. Etching at lower temperatures such as, for example, less than about 5° C., can be used to obtain higher levels of porosity.

Once porous silicon is formed, the inter-pore region is depleted of holes. Further dissolution should occur only at tips of the pores, where holes are still available. The dissolution of the silicon atoms is mainly restricted to the silicon/electrolyte interface and, therefore, the porous layer first formed should remain intact throughout subsequent etching. In this way, the etching of porous silicon proceeds in depth with an overall directionality that should follow the anodic current paths inside the silicon substrate. Multilayer structures typically are fabricated using a periodic current density square pulse during the electrochemical dissolution process. By pulsing between two different current densities, two different porosity porous silicon layers can be formed. For example, two different current densities, one of which is at about 5 milliamps per square centimeter ($mA/cm^2$) for 20 second period, and another of which is at 30 $mA/cm^2$ for a period of about 10 seconds, can be pulsed five times to produce 10 different layers of porous silicon.

The porosity is a linear function of the current density for a specific HF concentration and current density interval. Porosity values can be estimated using a porosity dependence on current density plot, and values for the thickness can be obtained through scanning electron microscope micrographs. For fixed values of porosities or refractive indices, the reflectivity of a multilayer substrate increases as the number of periods increases. Thus, for example, for a multilayer porous silicon substrate containing 6 periods, 88% reflectivity centered at 760 nm is attainable, and nearly 100% reflectivity is attainable for a multilayer porous silicon substrate containing 10 periods. Additional layers may be formed by employing additional current densities and appropriate pulsing.

After anodization, the porous silicon multilayer structures typically are stabilized by thermal oxidation in an oxygen atmosphere (ambient) at about 800° C. to about 1000° C. for about 5 minutes to about 20 minutes, preferably at about 850° C. to about 950° C. for about 8 minutes to about 15 minutes, more preferably at about 900° C. for about 10 minutes. Oxidation can induce a blue-shift in peak reflectivity due to a change in the refractive index of the layers. See generally, Moreno (1997) *Appl. Phys. Lett.*, 71:2166-2168. For multilayer structures, it has been found that the peak reflectivity may not decrease upon thermal treatment.

Another technique by which porous silicon can be made is "spark erosion." Spark erosion is a dry technique in that it does not utilize aqueous solutions or hydrofluoric acid for sample preparation. In contrast to anodic, electrochemical etching, n- or p-type silicon wafers are subjected to high frequency/low current electric sparks. A counter electrode is constructed of the same material as the wafer to avoid any unintended contamination of the wafer, and the technique is carried out in air, or in a dried, high purity nitrogen atmosphere to reduce or prevent hydrogen involvement. Spark erosion treatment of single crystalline silicon wafers produces randomly oriented silicon nanocrystallites imbedded in a silica matrix. High-energy electric sparks cause localized redeposition of silicon leading eventually to nanometer size crystallites. See generally, Hummel et al. (1993) *Appl. Phys. Lett.* 63:2771-2773. For a general description of anodic, electrochemical etching techniques for making multilayer porous silicon substrates, reference should be made to Chan et al. (2000) *Proc. of SPIE* 3912:23-34, the disclosure.

Porous silicon structures on a nanoscale can be made by an anisotropic etch with a solution of potassium hydroxide, for example, followed by high-temperature oxidation and oxide removal as described above. Such structures have silicon pillars having diameters less than about 10 nm and an aspect ratio of height to diameter as high as about 50:1. See generally, Nassiopoulus et al. (1995) *J. Phys. Stat. Sol.* 190:91-95; see also Zaidi et al. (1995) *Mat. Res. Soc. Symp. Proc.* 358:957-968.

Miniaturized Spectroscopy System

Micro-Electro-Mechanical Systems (MEMS) integrate mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible micromachining processes that selectively etch away parts of the silicon wafer or add new structural layers to form the mechanical and electromechanical devices. Microelectronic integrated circuits can be thought of as the brains of a system and MEMS augments this decision-making capability with eyes and arms, to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, functionality, reliability, and sophistication can be placed on a small silicon chip at a relatively low cost.

A sample to be analyzed can be delivered to a miniaturized spectroscopy device or optical detector using a microfluidic channel embedded in the system. Alternatively, the microfluidic channels can be part of a chip that can take the sample as an input, perform reactions, and then direct the sample for analysis.

Referring now to FIG. 1, a schematic of a miniaturized spectroscopy system that can be used for Raman spectroscopy and fluorescence detection applications is provided. In FIG. 1, porous silicon microcavity absorbs broadband light emitted from an inexpensive light source 1, such as for example, a green or blue LED, or a halogen, xenon, or mercury lamp. The porous silicon mircrocavity 5 emits light in a narrow band 7 of wavelengths. The sample receives the directional and narrowband light 7, and emits or scatters light 13 specific to the properties of the sample (e.g. fluorescence or Raman). A narrow band filter 15 is placed to block the excitation light 7 (the narrowband light from the porous silicon microcavity) and transmit only the light emitted by the sample 13. The narrow band filter can be a tunable liquid crystal filter or a Fabry-Perot interferometer (or a porous silicon filter). The Fabry-Perot interferometer can be fabricated by placing reflectors (e.g. partial mirrors or porous silicon layers) on a driving arm (the Fabry-Perot interferometer can also be made of porous silicon). Optical components, such as for example, mirrors and filters can also be fabricated from porous silicon.

Depending on the application, the sample chamber 9 can be a microfluidic channel in a silicon dioxide or polymer (for example, PDMS) or an array on a transparent substrate 11. Optionally the transparent substrate is removable. In the case of an array, a large-area porous silicon light source or multiple porous silicon light sources can be fabricated. The multiple porous silicon light sources can emit at the same wavelength or different wavelengths depending on the application. Additionally, a device can be created having a plurality of porous silicon light sources along one or more sample chambers having corresponding detectors. The plurality of porous silicon light sources can emit at the same or different wave lengths. The sample chamber has an inlet for receiving fluidic sample to be analyzed and an outlet for allowing sample to be removed from the chamber.

An array is an intentionally created collection of molecules which can be prepared either mechanically or synthetically. The molecules in the array can be identical or different from each other. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

The detector 17 can have single-pixel or multiple-pixels. Such detectors can include CCD array, CMOS detector array, photodiode, avalanche photodiode. The signal from the detector is read out sequentially by an electronic circuit to construct a spectrum.

Fourier transform spectroscopy is a measurement technique whereby spectra are collected based on the response from a pulse of electromagnetic radiation. It can be applied to variety of types of spectroscopy including infrared (FTIR), nuclear magnetic resonance, and electron spin resonance spectroscopy. Fourier transform spectroscopy can be more sensitive and has a much shorter sampling time than conventional spectroscopic techniques.

The detector 17 can optionally be an analyzer that would function as a miniaturized Fourier transforming spectrometer comprising an interferometer comprising waveguides. The analyzer could comprise an interferometer, a detector and a microprocessor, wherein the analyzer does not contain a spectrometer having a dispersive grating, the interferometer is to create a phase shift in an original spectrum of electromagnetic radiation emitted from a sample and Fourier transform the original spectrum to a Fourier transform spectrum, the detector is to detect a characteristic of the Fourier transform spectrum, and the microprocessor comprises software or a hardware to inverse transform the Fourier transform spectrum and reproduce the original spectrum. After passing through a Michelson interferometer (FIG. 4) or a Mach-Zehnder interferometer (MZI) (as shown in FIG. 5), the intensity of the electromagnetic radiation is measured as a function of phase shift. The phase is varied to obtain the Fourier transform of the spectrum. The characteristic could be wavelength, frequency, wave number, amplitude or any other property of the spectrum of electromagnetic radiation (e.g., light).

Figure 4:
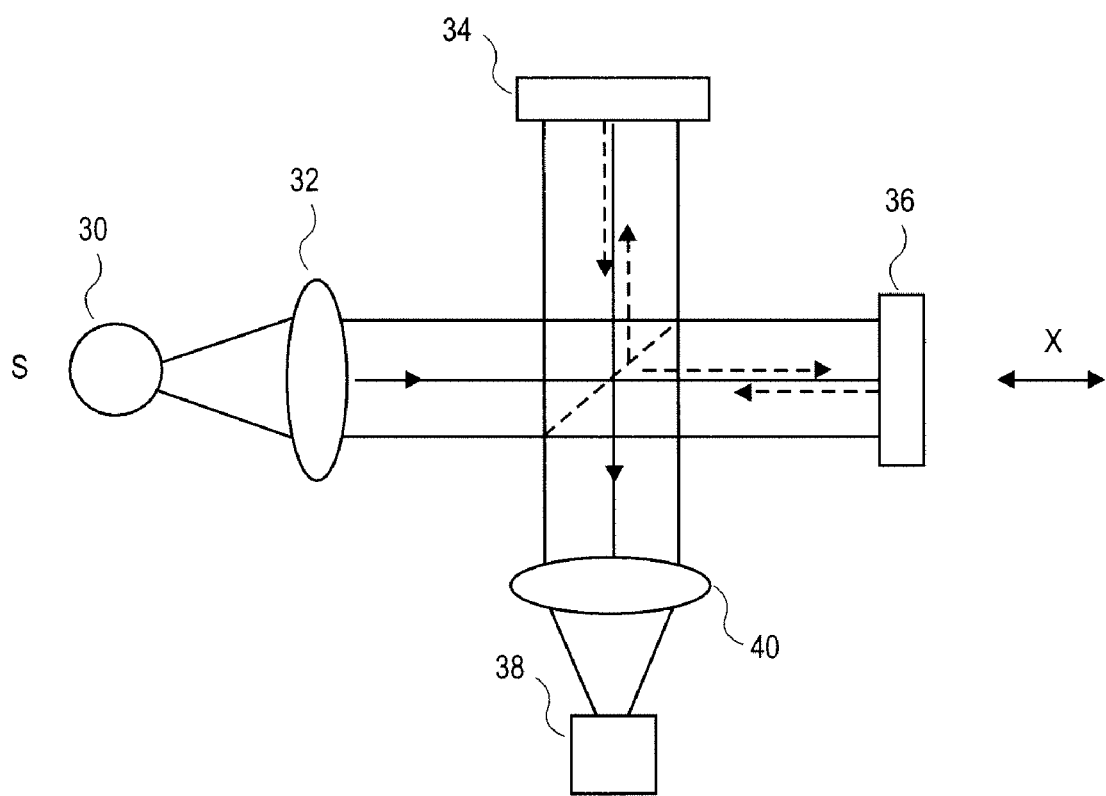
FIG. 4 shows a Fourier-transform infrared spectrometer (FTIR) based on Michelson interferometer.
Figure 5:
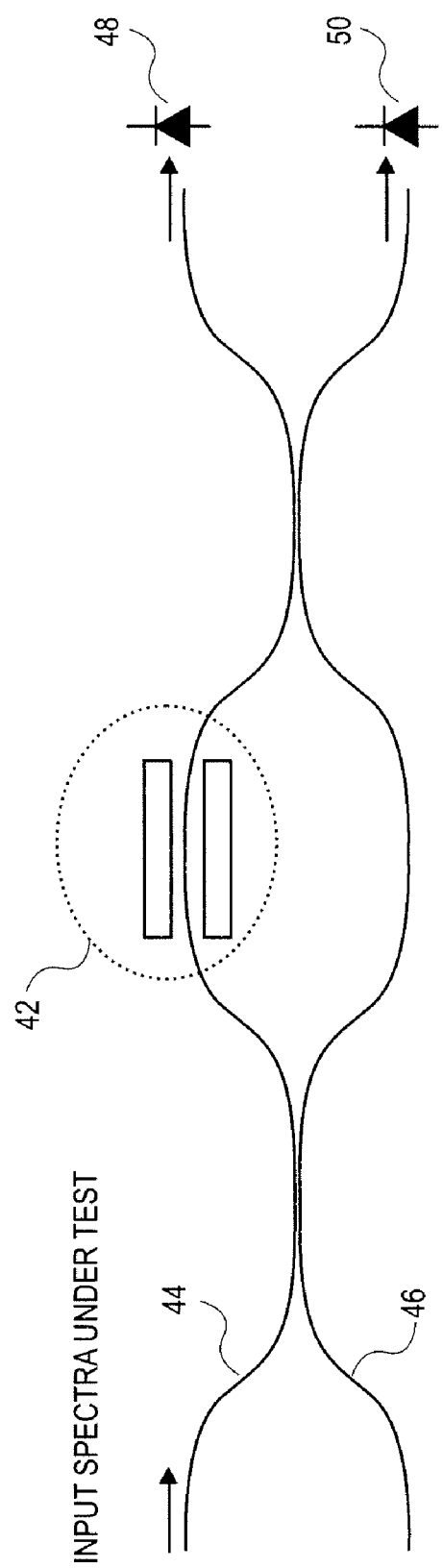
FIG. 5 shows an embodiment of a Mach-Zehnder interferometer (MZI).

Referring now to FIG. 4, a miniaturized Michelson interferometer with a micro-electro-mechanical-system (MEMS) based moving arm is shown. Multiple folded mirrors can be used to increase the path length difference. Optionally, separated waveguides with a reference light source may pass through the same phase-shifter to monitor the phase shifting accurately. In FIG. 4, light from a IR light source 30 is focused through a lense 32 into the device having a fixed mirror 34 and a moveable mirror 36, and light is detected by a detector 38 after passing through lense 40.

The Mach-Zehnder interferometer (FIG. 5) is functionally similar to the Michelson interferometer of FIG. 4. However, instead of creating the phase delay by changing the path length difference as in the Michelson interferometer, in Mach-Zehnder interferometer a variable index-of-refraction material 42 (a phase shifter) could be put into one of the two beam paths 44 and 46. By carefully controlling the index-of-refraction of the material 42, different interference fringes could be formed, which can be recorded by a single channel detector 48 and 50 (for example, a photodiode detector), for example. The recorded signal could be computed (inverse Fourier transformed) by a microprocessor to obtain the spectrum. The above embodiments of the analyzer would not require a spectrometer having a dispersive grating or having any moving parts.

A detector converts an optical signal of the characteristic of the Fourier transform spectrum to an electrical signal. The detector could be a charge coupled analyzer, a transducer or a photodiode. The phase/intensity information as electrical signals generated by the detector is then read-to a microprocessor, which is the fourth stage of the analyzer. The microprocessor contains software or a hardware to inverse Fourier transform the Fourier transform spectrum into the original spectrum of light emitted by the sample, which could be a frequency/intensity or wavelength/intensity spectrum such as a Raman spectrum, for example.

Embodiments of the present invention may be fabricated using common semiconductor and MEMS device fabrication techniques. The spectroscopy system could be synthesized on a silicon wafer or parts of the spectroscopy system could be synthesized independently and bonded together.

Embodiments of the present invention may be used to detect the presence of a particular target analyte. Target analytes may include, bio-derived materials, such as for example, nucleic acids, polynucleotides and oligonucleotides, polysaccharides, peptides, proteins, receptors, activators, repressors, histones, enzymes, antibodies, antigens, or combinations thereof. Such molecules and combinations include components of bacteria, viruses, chromosomes, genes, mitochondria, nuclei, cell membranes, and the like. The methods may also be used to screen bioactive agents, such as, for example, drug candidates, for binding to a particular target or to detect agents like drugs, metabolites, and pollutants. Further, analytes can be a cell or a part of a cell such as, a bacterium or a cell bearing a blood group antigen such as A, B, D, etc., or an HLA antigen or a microorganism, e.g., bacterium, fungus, protozoan, or virus.

An analyte can be in the solid, liquid, gaseous or vapor phase. By gaseous or vapor phase analyte is meant a molecule or compound that is present, for example, in the headspace of a liquid, in ambient air, in a breath sample, in a gas, or as a contaminant in any of the foregoing. The physical state of the gas or vapor phase can be changed by pressure, temperature as well as by affecting surface tension of a liquid by the presence of or addition of salts.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

Specific binding is the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—enzyme converted substrate interactions, polynucleotide hybridization interactions, and so forth.

The term probe or probe molecule refers to a molecule that specifically binds to a target molecule. The probe or probe molecule is generally, but not necessarily, has a known molecular structure or sequence. The probe or probe molecule is typically a nucleotide, an oligonucleotide, a protein, such as for example an antibody, or an antigen. Probes molecules are biomolecules capable of undergoing binding or molecular recognition events with target molecules. The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism.

Figure 6:
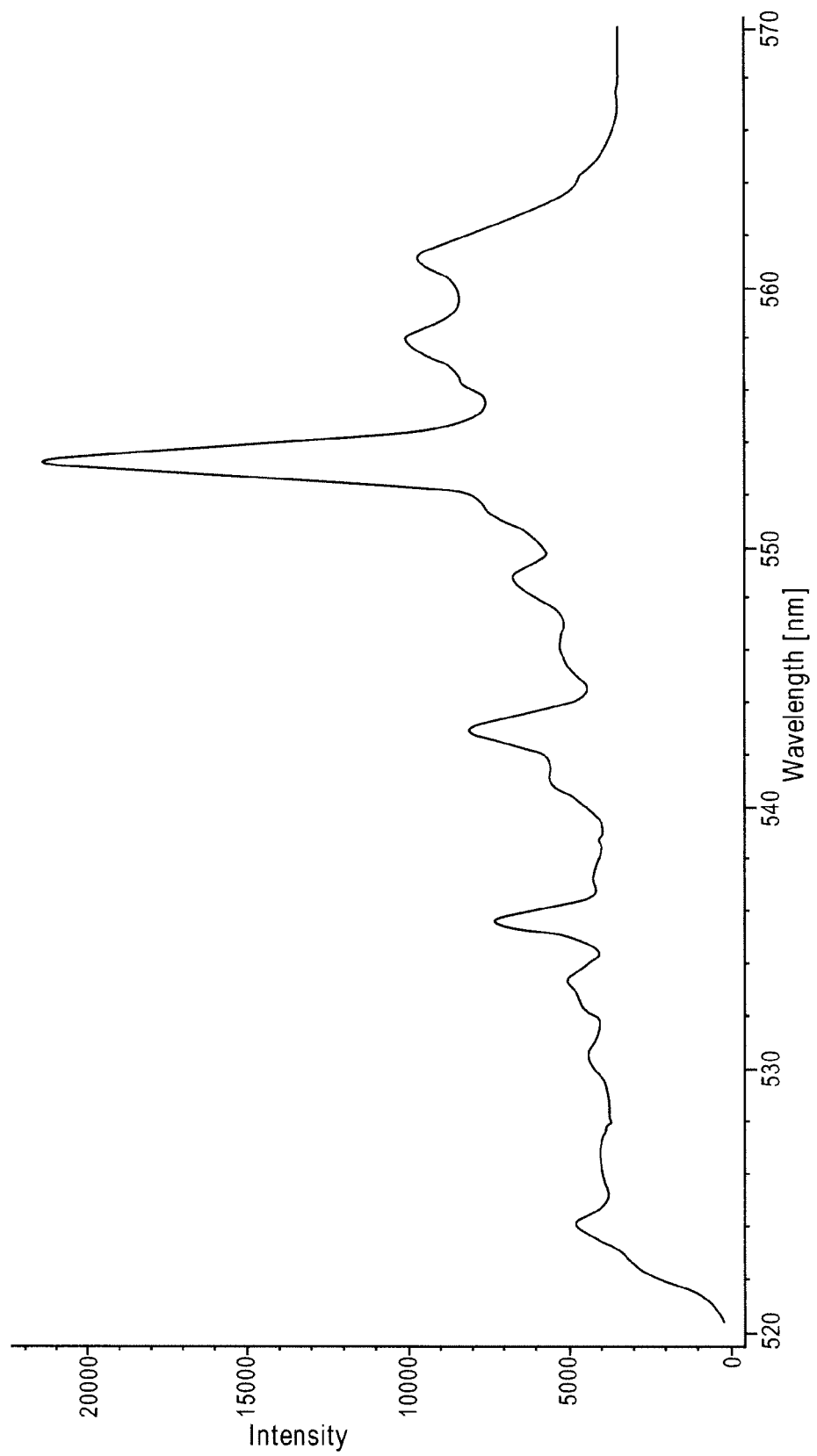
FIG. 6 shows a Raman spectrum obtained from an exemplary nanoparticle (COIN) that can be used as a reporter to detect the presence of one or more analytes in a sample.

Exemplary reporters for analyte detection include composite organic inorganic nanoclusters (COINs). COINs are composed of a metal and at least one organic Raman-active compound. Interactions between the metal of the clusters and the Raman-active compound(s) enhance the Raman signal obtained from the Raman-active compound(s) when the nanoparticle is excited by a laser. Since a large variety of organic Raman-active compounds can be incorporated into the nanoclusters, a set of COINs can be created in which each member of the set has a Raman signature unique to the set. Thus, COINs can also function as sensitive reporters for highly parallel analyte detection. Furthermore, not only are the intrinsic enhanced Raman signatures of the nanoparticles of the present invention sensitive reporters, but sensitivity may also be further enhanced by incorporating thousands of Raman labels into a single nanocluster and/or attaching multiple nanoclusters to a single analyte. Not only can COINS be synthesized with different Raman labels, but COINs may also be created having different mixtures of Raman labels and also different ratios of Raman labels within the mixtures. In general, Raman-active organic compound refers to an organic molecule that produces a unique SERS signature in response to excitation by a laser. Exemplary Raman-active organic compounds include, but are not limited to, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, 9-amino-acridine, and the like. Additional, non-limiting examples of Raman-active organic compounds include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like. These and other Raman-active organic compounds may be obtained from commercial sources (such as, for example, Molecular Probes, Eugene, Oreg.). FIG. 6 shows and exemplary COINs Raman spectrum.

In general, COINs can be prepared by causing colloidal metallic nanoparticles to aggregate in the presence of an organic Raman label. To prepare the colloidal metal nanoparticles, an aqueous solution is prepared containing suitable metal cations and a reducing agent. The components of the solution are then subject to conditions that reduce the metallic cations to form neutral, colloidal metal particles. It was found that aggregated metal colloids fused at elevated temperature and that organic Raman labels could be incorporated into the coalescing metal particles. These coalesced metal particles form stable clusters to produce intrinsically enhanced Raman scattering signals for the incorporated organic label. The Raman-active organic compound is readily incorporated onto the metal nanocluster during colloid formation. It is believed that the organic compounds trapped in the junctions between the primary metal particles provide the strongest Raman signal. Typical metals contemplated for use in formation of nanoparticles from metal colloids include, for example, silver, gold, copper, platinum, palladium, aluminum, gallium, indium, rhodium, and the like. The resulting COIN is typically less than 200 nm in diameter.

Optionally, COINs may be coated with metal layers, adsorption layers, silica layers, hematite layers, organic layers, and organic thiol-containing layers. Typically, the metal layer is different from the metal used to form the COIN. Additionally, a metal layer can typically be placed underneath any of the other types of layers. Many of the layers, such as the adsorption layers and the organic layers provide additional mechanisms for probe attachment. For instance, layers presenting carboxylic acid functional groups allow the covalent coupling of a biological probe, such as an antibody, through an amine group on the antibody.

COINs can be coated with an adsorbed layer of protein. Suitable proteins include non-enzymatic soluble globular or fibrous proteins. For applications involving molecular detection, the protein should be chosen so that it does not interfere with a detection assay, in other words, the proteins should not also function as competing or interfering probes in a user-defined assay. By non-enzymatic proteins is meant molecules that do not ordinarily function as biological catalysts. Examples of suitable proteins include avidin, streptavidin, bovine serum albumen (BSA), transferrin, insulin, soybean protein, casine, gelatine, and the like, and mixtures thereof. For example, a layer of BSA, not only contributes to the stability of the COIN, but it also provides additional mechanisms for probe attachment. The bovine serum albumen layer affords several potential functional groups, such as, carboxylic acids, amines, and thiols, for further functionalization or probe attachment. Optionally, the protein layer can be cross-linked with EDC, or with glutaraldehyde followed by reduction with sodium borohydride.

A COIN having an attached probe specific for the analyte, in this case an antibody that recognizes an epitope of the analyte, is then contacted with a sample solution under conditions that allow the COIN-antibody conjugate to bind to the analyte. Unbound COINs are then removed. The detection of the Raman signature of a COIN indicates the presence of the analyte in the analysis sample. This analysis can also be performed in a multiplexed fashion. A set of COINs can be created having unique signatures and probes specific for two or more known analytes in a sample. In this case the detection of each unique COIN signal is indicative of the presence of a specific known analyte in the analysis sample.

We claim:

1. A spectroscopy device comprising:
   a porous silicon light emitting microcavity;
   a sample chamber oriented to receive light emitted from the porous silicon light emitting microcavity;
   a narrowband transmission filter oriented to transmit light from the sample chamber; and
   a detector oriented to receive light transmitted by the narrow band transmission filter.

2. The device of claim 1 wherein the porous silicon light emitting microcavity is a photoluminescent emitter capable of absorbing broadband light.

3. The device of claim 1 wherein the porous silicon light emitting microcavity is an electroluminescent emitter.

4. The device of claim 1 wherein the narrowband transmission filter is a liquid crystal filter.

5. The device of claim 1 wherein the narrowband transmission filter is a Fabry-Perot filter comprised of porous silicon or doped porous silicon.

6. The device of claim 1 wherein the porous silicon light emitting cavity is comprised of three or more layers of doped or undoped porous silicon.

7. The device of claim 6 wherein the porous silicon light emitting cavity has an interior layer of luminescent porous silicon.

8. The device of claim 1 wherein the detector is selected from the group consisting of CCD arrays, CMOS detector arrays, photodiodes, and avalanche photodiodes.

9. The device of claim 1 wherein the porous silicon light emitting microcavity, the sample chamber, and the narrowband transmission filter are fabricated from a silicon substrate.

10. A method for analyzing a sample comprising:
    striking the sample with electromagnetic radiation emitted from a porous silicon microcavity to produce a Raman or a fluorescence emission from the sample;
    filtering the emission from the sample through a transmission filter that is capable of transmitting emission from the sample; and
    detecting the emission from the sample.

11. The method of claim 10 wherein the sample is located in a microfluidic channel.

12. The method of claim 10 wherein the sample is an array located on a transparent substrate.

13. The method of claim 10 wherein the transmission filter is a liquid crystal filter.

14. The method of claim 10 wherein the transmission filter is a Fabry-Perot filter comprised of porous silicon or doped porous silicon.

15. The method of claim 10 wherein the detector is selected from the group consisting of CCD arrays, CMOS detector arrays, photodiodes, and avalanche photodiodes.

16. The method of claim 10 wherein the porous silicon light emitting cavity is comprised of three or more layers of doped and undoped porous silicon.

17. The method of claim 16 wherein the porous silicon light emitting cavity has an interior layer of luminescent porous silicon.

18. The method of claim 10 wherein the emission is a Raman emission from a composite organic inorganic nanocluster.

19. The method of claim 18 also comprising mixing the sample with a solution containing composite organic inorganic nanoclusters having an attached probe specific for an analyte in the sample under conditions that allow the probe to specifically attach to the analyte and removing any nanocluster that are not bound to an analyte.

20. The method of claim 10 wherein the method is repeated a plurality of times to detect a plurality of analytes that emit light at different wavelengths.

21. The method of claim 10 wherein detecting emission from the sample includes obtaining an FTIR spectrum of the sample.

* * * * *

UNITED STATES PATENT AND TRADEMARK OFFICE
CERTIFICATE OF CORRECTION

PATENT NO. : 7,330,252 B2  Page 1 of 1
APPLICATION NO. : 11/325832
DATED : February 12, 2008
INVENTOR(S) : Koo et al.

It is certified that error appears in the above-identified patent and that said Letters Patent is hereby corrected as shown below:

Col. 52, at line 7, delete "spectros copy" and insert --spectroscopy--.

Signed and Sealed this

Twenty-sixth Day of August, 2008

JON W. DUDAS
*Director of the United States Patent and Trademark Office*